(12) United States Patent
Kanatani et al.

(10) Patent No.: US 9,433,211 B2
(45) Date of Patent: Sep. 6, 2016

(54) ANTIMICROBIAL AGENT

(75) Inventors: Shuji Kanatani, Osaka (JP); Soota Iwamoto, Osaka (JP)

(73) Assignee: TAIYO CORPORATION, Osaka (JP)

( * ) Notice: Subject to any disclaimer, the term of this patent is extended or adjusted under 35 U.S.C. 154(b) by 0 days.

(21) Appl. No.: 14/363,461

(22) PCT Filed: Feb. 13, 2012

(86) PCT No.: PCT/JP2012/053229
§ 371 (c)(1),
(2), (4) Date: Sep. 16, 2014

(87) PCT Pub. No.: WO2013/121501
PCT Pub. Date: Aug. 22, 2013

(65) Prior Publication Data
US 2015/0005378 A1   Jan. 1, 2015

(51) Int. Cl.
| | |
|---|---|
| *A01N 37/02* | (2006.01) |
| *A61K 31/23* | (2006.01) |
| *C07C 69/66* | (2006.01) |
| *A01N 37/36* | (2006.01) |
| *A61K 8/37* | (2006.01) |
| *A61Q 19/00* | (2006.01) |
| *C07C 69/675* | (2006.01) |
| *A61Q 17/00* | (2006.01) |
| *A61Q 7/00* | (2006.01) |

(52) U.S. Cl.
CPC ............... *A01N 37/36* (2013.01); *A61K 8/37* (2013.01); *A61K 8/375* (2013.01); *A61Q 17/005* (2013.01); *A61Q 19/007* (2013.01); *C07C 69/675* (2013.01); *A61K 2800/10* (2013.01); *A61K 2800/524* (2013.01); *A61K 2800/74* (2013.01); *A61Q 7/00* (2013.01)

(58) Field of Classification Search
USPC .......................................... 514/552; 560/179
See application file for complete search history.

(56) References Cited

FOREIGN PATENT DOCUMENTS

| CN | 101137357 A | 9/2006 |
|---|---|---|
| CN | 101137357 | 3/2008 |
| CN | 101137357 A | 3/2008 |
| JP | S48-96720 | 12/1973 |
| JP | H8-325107 | 12/1996 |
| JP | H11-322691 | 11/1999 |
| JP | 2008-537732 | 9/2008 |
| JP | 2010-180137 | 8/2010 |
| JP | 2010-180137 A | 8/2010 |
| JP | 2010180137 A | 8/2010 |
| JP | 2012-56893 | 3/2012 |
| WO | 2006099358 A2 | 9/2006 |

OTHER PUBLICATIONS

Official Action dated Mar. 2, 2015 issued in connection with corresponding Chinese Patent Application No. 201280067067.6. 6 pages, with English translation.
Official Action issued on Oct. 13, 2015 in connection with corresponding Chinese Patent Application No. 201280067067.6, along with its English translation.
Third Office Action dated Mar. 15, 2016 issued in connection with corresponding Chinese Patent Application No. 201280067067.6 with English translation.

*Primary Examiner* — Marcos Sznaidman
(74) *Attorney, Agent, or Firm* — Vedder Price, P.C.

(57) ABSTRACT

[Problem] To provide a novel antimicrobial agent that has excellent antimicrobial activity and which is prepared from an ester composed of propanediol and a β-hydroxycarboxylic acid.

[Solution] An antimicrobial agent which is prepared from a propanediol mono-β-hydroxycarboxylic acid ester expressed by the following formula (1) or formula (2) (wherein $R^1$ and $R^2$ are both branched or unbranched, and saturated or unsaturated alkyl groups having 5 to 9 carbon atoms).

[Chemical formula 1]

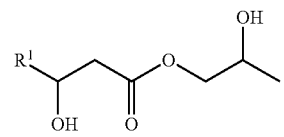

(1)

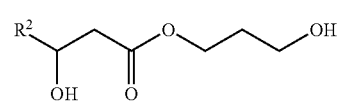

(2)

9 Claims, 1 Drawing Sheet

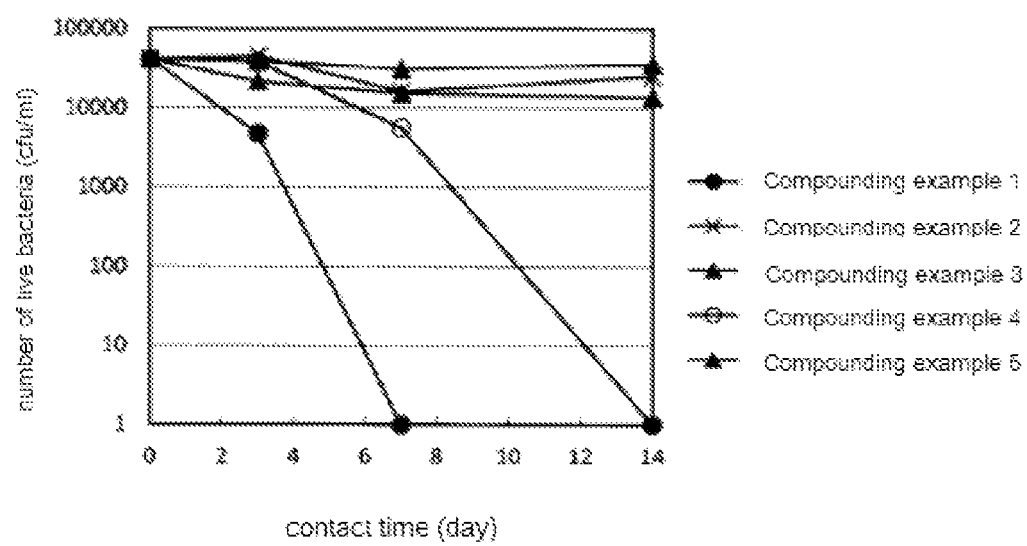

ANTIMICROBIAL AGENT

BACKGROUND OF THE INVENTION

1. Field of the Invention

The present invention relates to an antimicrobial agent, in particular, an antimicrobial agent which is prepared from a propanediol mono-β-hydroxycarboxylic acid ester which is an ester composed of propanediol and β-hydroxycarboxylic acid.

2. Description of the Related Art

In recent years, skin irritation caused by paraben has become a problem and it is desired to reduce the compounding amount of this substance for safety sake. As a technique for reducing or excluding antiseptic bactericides such as paraben, benzoic acids and salicylic acids which are used as antiseptic bactericides of cosmetic products and pharmaceutical products, there has been disclosed an antiseptic bactericide which is prepared from 1,2-alkanediol (refer to Patent Document 1). However, if 1,2-alkanediol such as 1,2-octanediol is used solely as an antiseptic bactericide, compounding a large amount of this substance might be required in order to obtain sufficient effects. Further, 1,2-alkanediol has a distinctive odor derived a raw material. Thus, it is desired to develop an antiseptic bactericide which is capable of exerting sufficient antiseptic and bactericidal effects.

It is also known that an ester of hydroxycarboxylic acid exhibits antimicrobial actions. For example, there have been disclosed an antimicrobial agent which is characterized in containing an α-hydroxycarboxylic acid alkyl ester as an effective component and a cosmetic product which contains an optically active α-hydroxycarboxylic acid alkyl ester as an antimicrobial component (refer to Patent Document 2).

However, any of the hydroxycarboxylic acid which is a constituent component of the above-described hydroxycarboxylic acid ester is that having a hydroxyl group at the alpha position and there is no disclosure about β-hydroxycarboxylic acid having a hydroxyl group at the beta position. Further, disclosed is an alkyl ester with monovalent alcohol having one hydroxyl group, and there is no disclosure about a monoester with polyvalent alcohol such as propanediol. Further, there has been a problem with a hydroxycarboxylic acid alkyl ester that it has a lower affinity to water than a monoester made up of hydroxycarboxylic acid and polyvalent alcohol due to having less hydroxyl groups.

Patent Document 1: Japanese Published Unexamined Patent Application No. H11-322591

Patent Document 2: Japanese Published Unexamined Patent Application No. H8-325107

SUMMARY OF THE INVENTION

The present invention has been made in view of the above-described circumstances, a main purpose of which is to provide a new antimicrobial agent which is prepared from an ester composed of propanediol and β-hydroxycarboxylic acid and which is excellent in antimicrobial activity.

As a result of intensively conducting studies to accomplish the above purpose, the present inventors found that an ester composed of propanediol and β-hydroxycarboxylic acid has excellent antimicrobial activity against bacteria such as molds and yeasts, thereby completing the present invention.

That is, the present invention is summarized as follows:

[1] The formula (1) or the formula (2) given below:

[Chemical formula 1]

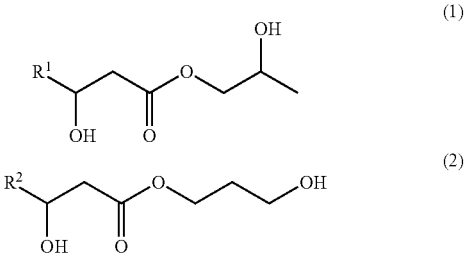

An antimicrobial agent which is prepared from a propanediol mono-β-hydroxycarboxylic acid ester expressed by the above formula (wherein $R^1$ and $R^2$ are both branched or unbranched, and saturated or unsaturated alkyl groups having 5 to 9 carbon atoms).

[2] The antimicrobial agent which is described in the above [1], wherein $R^1$ and $R^2$ are both unbranched, and saturated or unsaturated alkyl groups having 7 to 9 carbon atoms.

[3] A cosmetic product which contains the antimicrobial agent described in the above [1] or [2].

[4] A method for compounding the antimicrobial agent described in the above [1] or [2] into an item to be antisepticized, thereby enhancing antiseptic effects on the item to be antisepticized.

The antimicrobial agent of the present invention is prepared from a specific propanediol mono-β-hydroxycarboxylic acid ester and exhibits excellent antimicrobial activity against fungi such as molds and yeasts. Therefore, the antimicrobial agent is compounded into an item to be antisepticized, thus making it possible to enhance antiseptic effects on the item to be antisepticized.

BRIEF DESCRIPTION OF THE DRAWINGS

FIG. 1 is a drawing which shows changes in the number of bacteria remaining in test samples with the lapse of time.

DETAILED DESCRIPTION OF THE PREFERRED EMBODIMENTS

As described above, the antimicrobial agent of the present invention is characterized in being prepared from a propanediol mono-β-hydroxycarboxylic acid ester which is an ester composed of propanediol and β-hydroxycarboxylic acid.

Specifically, the antimicrobial agent includes an ester which is composed of 1,2-propanediol and β-hydroxycarboxylic acid, that is, a propanediol mono-β-hydroxycarboxylic acid ester expressed by the formula (1) given below:

[Chemical formula 2]

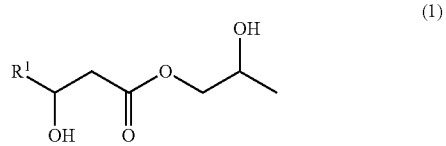

(wherein R¹ represents a branched or unbranched, and saturated or unsaturated alkyl group having 5 to 9 carbon atoms) or an ester which is composed of 1,3-propanediol and β-hydroxycarboxylic acid, that is, a propanediol mono-β-hydroxycarboxylic acid ester which is expressed by the formula (2) given below.

[Chemical formula 3]

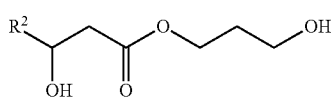

(2)

(wherein R² represents a branched or unbranched, and saturated or unsaturated alkyl group having 5 to 9 carbon atoms).

Of the above-described propanediol mono-β-hydroxycarboxylic acid esters, in terms of particularly excellent antimicrobial activity, an unbranched, and saturated or unsaturated alkyl group having 7 to 9 carbon atoms is more preferable as R¹ and an unbranched, and saturated or unsaturated alkyl group having 7 to 9 carbon atoms is more preferable as R², as with R¹. Specifically, those which are composed of 1,2-propanediol include a 1,2-propanediol mono-β-hydroxydecanoic acid ester (the present invention product 3 as an example to be described later) which is expressed by the formula (3) given below in which R¹ has 7 carbon atoms, a 1,2-propanediol mono-β-hydroxyundecanoic acid ester (the present invention product 2 as an example to be described later) which is expressed by the formula (4) given below in which R¹ has 8 carbon atoms, and a 1,2-propanediol mono-β-hydroxydodecanoic acid ester (the present invention product 1 as an example to be described later) which is expressed by the formula (5) given below in which R¹ has 9 carbon atoms.

[Chemical formula 4]

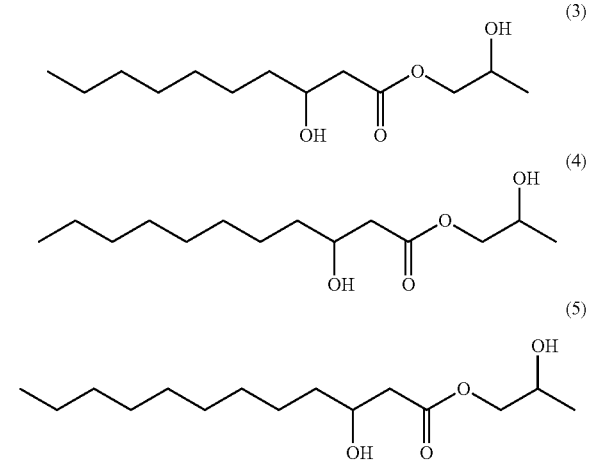

Further, those which are composed of 1,3-propanediol include a 1,3-propanediol mono-β-hydroxydecanoic acid ester (the present invention product 8 as an example to be described later) which is expressed by the formula (6) given below in which R² has 7 carbon atoms, a 1,3-propanediol mono-β-hydroxyundecanoic acid ester (the present invention product 7 as an example to be described later) which is expressed by the formula (7) given below in which R² has 8 carbon atoms, and a 1,3-propanediol mono-β-hydroxydodecanoic acid ester (the present invention product 6 as an example to be described later) which is expressed by the formula (8) given below in which R² has 9 carbon atoms.

[Chemical formula 5]

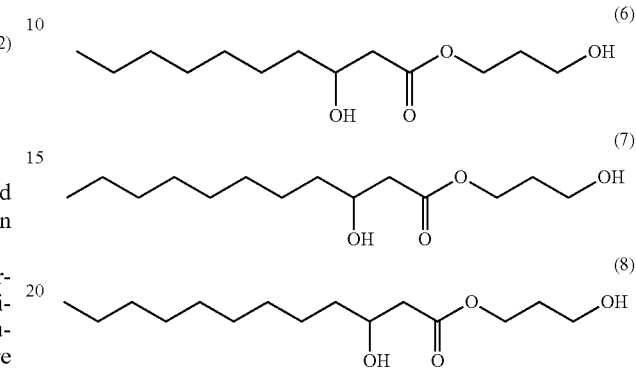

With regard to β-hydroxycarboxylic acids, each of which is a component of the above-described ester, those with an unbranched and saturated alkyl group in which R¹ or R² has to 9 carbon atoms include, for example, β-hydroxyoctanoic acid, β-hydroxynonanoic acid, β-hydroxydecanoic acid, β-hydroxyundecanoic acid and β-hydroxydodecanoic acid. Further, those with an unbranched and unsaturated alkyl group in which R¹ or R² has 5 to 9 carbon atoms include, for example, β-hydroxy-5-octenoic acid, β-hydroxy-5-nonenoic acid, β-hydroxy-5-decenoic acid, β-hydroxy-5-undecenoic acid and β-hydroxy-5-dodecenoic acid.

The antimicrobial agent of the present invention is produced by enzyme reactions of 1,2-propanediol or 1,3-propanediol with the above-described specific β-hydroxycarboxylic acid or its derivative (for example, lipase is used as an enzyme) or by chemical synthesis by which esterification or ester exchange takes place (hereinafter, collectively referred to as "esterification"). Moreover, a β-hydroxycarboxylic acid or its derivative used for the esterification can be produced, for example, by Knoevenagel condensation, Darzens condensation, Reformatsky reaction, etc. Of these methods, Reformatsky reaction is usually employed in view of yield and by-products.

Hereinafter, as a method for producing the antimicrobial agent of the present invention, a specific description will be given of a method in which Reformatsky reaction is used to produce a β-hydroxycarboxylic acid ester, then, the ester and propanediol are subjected to ester exchange by using a lipase to produce a propanediol mono-β-hydroxycarboxylic acid ester.

In Reformatsky reaction, there is produced a β-hydroxycarboxylic acid ester by condensation reactions between an aldehyde with a branched or unbranched, and saturated or unsaturated alkyl group having 6 to 10 carbon atoms and, preferably, having 8 to 10 carbon atoms, and a bromoacetic acid ester. Specifically, aldehydes with an unbranched and saturated alkyl group having 6 to 10 carbon atoms include, for example, hexanal, heptanal, octanal, nonanal and decanal. The bromoacetic acid ester includes, for example, methyl bromoacetate, ethyl bromoacetate, propyl bromoacetate and butyl bromoacetate. Catalysts used in Reformatsky reaction include, for example, zinc, magnesium, and iron.

Secondly, ester exchange by using a lipase is explained below. Lipase used for ester exchange is not particularly limited, as long as it recognizes glycerides as a substrate. For example, monoglyceride lipase, cutinase, and esterase are included. Among them, lipase is preferable, and such lipase includes, for example, monoglyceride lipase and mono/diglyceride lipase.

A purified lipase (including a roughly purified or a partially purified lipase) may by used. Further, free lipase or lipase immobilized on a carrier such as ion exchange resin, a porous resin, ceramics calcium, or carbonate, may be used.

Methods for isolating and purifying a propanediol mono-β-hydroxycarboxylic acid ester from a reaction mixture solution include, for example, deacidification, rinsing, distillation, solvent extraction, ion-exchange chromatography, thin layer chromatography, and membrane separation. These methods are used solely or in combination.

In regard to the above-described methods for producing the antimicrobial agent of the present invention, an octanal and a methyl bromoacetate are used as starting materials to produce a β-hydroxydecanoic acid methyl ester through Reformatsky reaction and then the ester is allowed to react with a 1,2-propanediol or a 1,3-propanediol in the presence of a lipase, and ester exchange is performed to produce a 1,2-propanediol mono-β-hydroxydecanoic acid ester and a 1,3-propanediol mono-β-hydroxydecanoic acid ester. The production method is expressed by a chemical formula as the formula (9) given below.

products, medical devices, and industrial products. Cosmetics include perfume cosmetics. Pharmaceutical products include, for example, products equivalent to pharmaceutical products (for example, quasi drugs stipulated by the Pharmaceutical Affairs Act such as medical cosmetic products), in addition to external preparations for skin. Medical devices include, for example, oral hygiene products. Industrial products include, for example, tableware, clothing, paints, and pet hygiene products. The antimicrobial agent of the present invention is useful in enhancing antiseptic effects of cosmetics or pharmaceutical products in particular by being compounded into cosmetics or pharmaceutical products. The antimicrobial agent contained in an item to be antisepticized is generally in a range of 0.01 to 50 weight percent and preferably in a range of 0.1 to 10 weight percent.

When the antimicrobial agent of the present invention is compounded into the above-described item to be antisepticized, one type among the antimicrobial agent may be used solely and two or more types among the antimicrobial agent can be used in combination. The antimicrobial agent of the present invention may be combined with one or two or more other types of antimicrobial agents that are conventionally known. Other antimicrobial agents which can be combined include, for example, bactericides such as cetylpyridinium chloride, dequalinium chloride, benzalkonium chloride, chlorhexidine, triclosan, isopropyl methylphenol, ofloxacin, iodine, sodium fluoride, and benzoic acid-based, sorbic acid-based, organic halogen-based and benzimidazole-based

[Chemical formula 6]

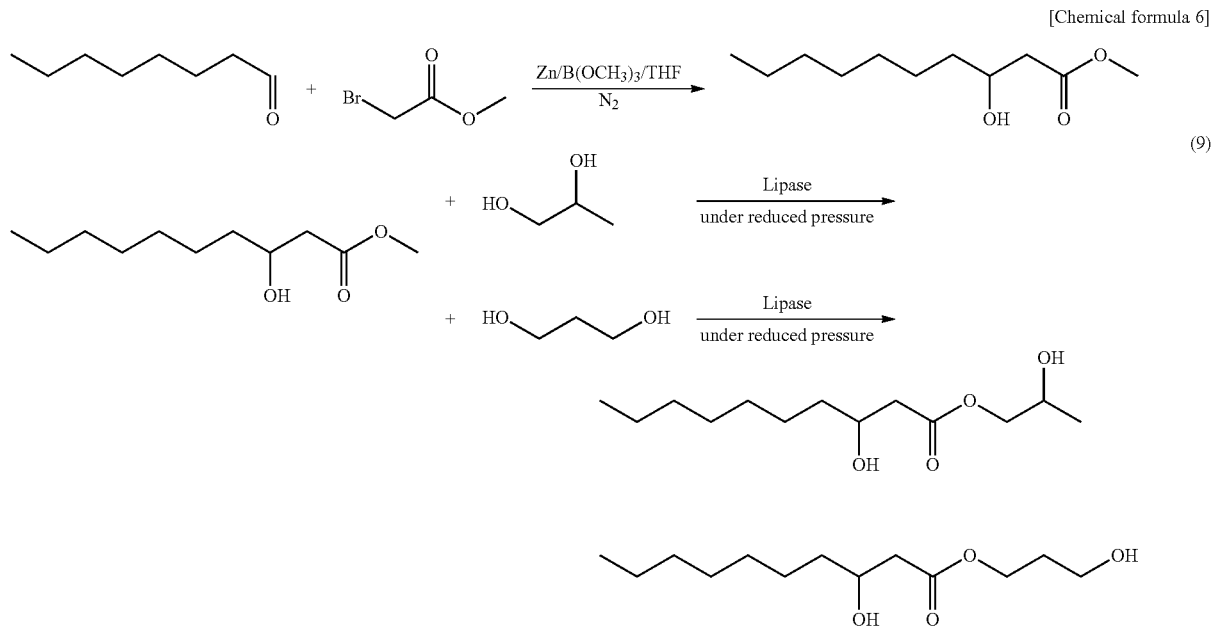

(9)

The antimicrobial agent of the present invention exhibits excellent antimicrobial activity against fungi such as yeasts and black mold. Therefore, the antimicrobial agent of the present invention is compounded into an item to be antisepticized, thus making it possible to enhance antiseptic effects on the item to be antisepticized. There is no restriction on the item to be antisepticized as long as it is a product in which an ordinary antiseptic or antimicrobial agent is compounded for the purpose of antisepsis (that is, for a non-therapeutic purpose). The item to be antisepticized includes, for example, foods, cosmetics, pharmaceutical microbicidal agents, metal ions such as silver and copper ions, as well as lecithin, sucrose fatty acid ester, glycerin fatty acid ester, polyoxyethylene sorbitan fatty acid ester, ethanol, propylene glycol, 1,2-alkanediol, polylysine, lysozyme, chitosan, thymol, eugenol, and plant extract such as an oil-based licorice extract, a mulberry root bark extract, an Angelica keiskei extract, spice extract, and polyphenol, etc. Furthermore, the antimicrobial agent of the present invention can be used by being mixed with general components of external preparations for skin.

A form of the antimicrobial agent of the present invention can be appropriately changed, depending on the above-described item to be antisepticized, and for example, a granular form, a paste form, a solid form, or a liquid form may be adopted.

When the antimicrobial agent of the present invention is compounded into the above-described item to be antisepticized, any publicly known apparatus (a paddle mixer, a homomixer, and a homogenizer, and the like) which can produce the above-described form may be preferably used. Since the antimicrobial agent of the present invention has an excellent compounding property, the antimicrobial agent is not separated out as a crystal from the produced various items to be antisepticized.

Examples

Although the present invention will be more specifically described below using test examples and others, these examples are not intended to limit the present invention.

A. Synthesis Examples of Various Types of Propanediol Mono-β-Hydroxycarboxylic Acid Esters and Others (1) Synthesis Examples of 1,2-Propanediol Mono-β-Hydroxycarboxylic Acid Ester (the Present Invention Product 1)

(1-1) Synthesis Example of β-Hydroxydodecanoic Acid Methyl Ester by Reformatsky Reaction 6.5 g of zinc, 15.5 g of decanal, 25 ml of trimethoxyborane, and 25 ml of dried THF were put into a 300 ml four-neck round-bottom flask, and 17.5 g of methyl bromoacetate was dripped at 20° C. for two hours in a nitrogen gas stream. After dripping, a resultant thereof was agitated at 20° C. for one hour, and thereafter, 25 ml of saturated ammonia aqueous solution and 25 ml of glycerin were added and agitated for ten minutes. An organic layer was separated and an aqueous solution layer was extracted two times by using diethyl ether. Thereafter, the organic solution was collected and subjected to desolvation. A residue thereof was purified by distillation to obtain a β-hydroxydodecanoic acid methyl ester.

(1-2) Synthesis Example of 1,2-Propanediol Mono-β-Hydroxydodecanoic Acid Ester

The thus obtained 5 g of β-hydroxydodecanoic acid methyl ester, 5 g of 1,2-propanediol, and 0.05 g of immobilized lipase (product name of Novozyme 435: Novozymes Japan Co., Ltd.) were added into a 50 ml pressure-resistant vial container and agitated at 50° C. for twenty-four hours under reduced pressure of 10 mmHg. After reaction, the thus obtained reaction solution was purified by silica gel column chromatography to obtain a 1,2-propanediol mono-β-hydroxydodecanoic acid ester with 99% purity (the present invention product 1).

(2) Synthesis Examples of 1,2-Propanediol Mono-β-Hydroxycarboxylic Acid Esters (the Present Invention Products 2 to 5)

Except that nonanal, octanal, heptanal and hexanal were used in place of decanal used in the above-description of (1) as an aldehyde, the same method as that of the above-description of (1) was employed to obtain respectively a 1,2-propanediol mono-β-hydroxyundecanoic acid ester (the present invention product 2), 1,2-propanediol mono-β-hydroxydecanoic acid ester (the present invention product 3), a 1,2-propanediol mono-β-hydroxynonanoic acid ester (the present invention product 4) and a 1,2-propanediol mono-β-hydroxyoctanoic acid ester (the present invention product 5). After reactions, reaction solutions of the thus obtained present invention products 2 to 5 were purified by silica gel column chromatography and it was found that the purity of each of the purified products was 99%.

(3) Synthesis Examples of 1,3-Propanediol Mono-β-Hydroxycarboxylic Acid Esters (the Present Invention Products 6 to 10)

Except that 1,3-propanediol was used in place of 1,2-propanediol used in the above descriptions of (1) and (2), the same method as that of the above descriptions of (1) and (2) was employed to obtain respectively a 1,3-propanediol mono-β-hydroxydodecanoic acid ester (the present invention product 6), 1,3-propanediol mono-β-hydroxyundecanoic acid ester (the present invention product 7), a 1,3-propanediol mono-β-hydroxydecanoic acid ester (the present invention product 8), a 1,3-propanediol mono-β-hydroxynonanoic acid ester (the present invention product 9) and a 1,3-propanediol mono-β-hydroxyoctanoic acid ester (the present invention product 10). After reactions, reaction solutions of the thus obtained present invention products 6 to 10 were purified by silica gel column chromatography to find that the purity of each of the purified products was 99%.

(4) Synthesis Example of Glycerin Mono β-Hydroxydecanoic Acid Ester (Comparative Product 1)

Except that glycerin and β-hydroxydecanoic acid methyl ester were used in place of 1,2-propanediol and β-hydroxydodecanoic acid methyl ester used in the above description of (1), the same method as that of the above description of (1) was employed to obtain glycerin mono β-hydroxydecanoic acid ester (comparative product 1). After reactions, a reaction solution of the thus obtained comparative product 1 was purified by silica gel column chromatography and it was found that the purity of each of the purified products was 99%.

(5) Synthesis Example of β-Hydroxydecanoic Acid Potassium (Comparative Product 2)

First, except that octanal was used in place of decanal used in the above description of (1), the same method as that of the above description of (1) was employed to obtain a β-hydroxydecanoic acid methyl ester. Secondly, the thus obtained 5 g of β-hydroxydecanoic acid methyl ester, 3 g of sodium hydroxide, 15 ml of water and 15 ml of ethanol were mixed in a 50 ml vial container and a resultant thereof was agitated at 70° C. for one hour. Thereafter, the resultant was acidified by addition of hydrochloric acid and extracted by diethyl ether. After desolvation, an ethanol solution containing an equivalent quantity of potassium hydroxide was added to the thus obtained β-hydroxydecanoic acid for neutralization. After removal of ethanol under reduced pressure, the resultant was dried to obtain β-hydroxydecanoic acid potassium (comparative product 2).

B. Verification Test of Antimicrobial Effects on Black Mold and Yeasts 0.5 ml of a previously sterilized culture medium (trade name "Potato dextrose liquid culture medium", made by Nissui Pharmaceutical Co., Ltd. was placed into a 96-well deep type microplate, then the propanediol mono-β-hydroxycarboxylic acid esters (the present invention products 1 to 10), the glycerin mono β-hydroxydecanoic acid ester (comparative product 1), the β-hydroxydecanoic acid potassium (comparative product 2) prepared in the above descriptions of (1) to (5) as well as 1,2-octanediol (comparative product 3), 1,2-propanediol (comparative product 4) and 1,3-propanediol (comparative product 5) known as an auxiliary antiseptic agent for external preparations for skin were respectively added, and the culture medium was diluted in a step-wise manner so that the final concentration in the medium was 156 ppm, 312 ppm, 625 ppm, 1250 ppm, and 2500 ppm to prepare sample solutions.

To these sample solutions, 0.1 ml of each culture solution of blackmold (*A. niger*, JCM10254) and yeast (*C. albicans*, NBRC1594) at approximately $1 \times 10^6$ CFU/ml were added, and the solutions were cultured at 30° C. under an aerobic condition for four days. Antimicrobial effects were visually determined. The solutions were compared with test areas in which the above microorganisms had not been added. Test areas in which no turbidity due to growth of the microorganism was observed were determined to have antimicrobial effects, and the lowest concentration necessary for inhibiting the growth of the microorganism (hereinafter referred to as "minimum inhibitory concentration") was measured. Table 1 shows the results.

TABLE 1

| Name of Component | | Minimum inhibitory concentration (ppm) | |
|---|---|---|---|
| | | *A. niger* | *C. albicans* |
| Present invention product 1 | 1,2-propanediol mono-β-hydroxydodecanoic acid ester | 312 | 312 |
| Present invention product 2 | 1,2-propanediol mono-β-hydroxyundecanoic acid ester | 312 | 312 |
| Present invention product 3 | 1,2-propanediol mono-β-hydroxydecanoic acid ester | 312 | 625 |
| Present invention product 4 | 1,2-propanediol mono-β-hydroxynonanoic acid ester | 1250 | 1250 |
| Present invention product 5 | 1,2-propanediol mono-β-hydroxyoctanoic acid ester | 2500 | >2500 |
| Present invention product 6 | 1,3-propanediol mono-β-hydroxydodecanoic acid ester | 156 | 312 |
| Present invention product 7 | 1,3-propanediol mono-β-hydroxyundecanoic acid ester | 312 | 312 |
| Present invention product 8 | 1,3-propanediol mono-β-hydroxydecanoic acid ester | 312 | 625 |
| Present invention product 9 | 1,3-propanediol mono-β-hydroxynonanoic acid ester | 1250 | 1250 |
| Present invention product 10 | 1,3-propanediol mono-β-hydroxyoctanoic acid ester | 2500 | >2500 |
| Comparative product 1 | Glycerin mono β-hydroxydecanoic acid ester | 2500 | >2500 |
| Comparative product 2 | β-hydroxydecanoic acid potassium | 1250 | 2500 |
| Comparative product 3 | 1,2-octanediol | 2500 | 2500 |
| Comparative product 4 | 1,2-propanediol | >2500 | >2500 |
| Comparative product 5 | 1,3-propanediol | >2500 | >2500 |

From the results in Table 1, it was found that the present invention products 1 to 10 exhibited antimicrobial activities equal to or greater than 1,2-octanediol (comparative product 3) used as a control against black mold (*A. niger*). The present invention products 1 to 10 tended to increase in antimicrobial activities with an increase in the carbon number of β-hydroxycarboxylic acid which was one component. However, no significant difference was found depending on whether propanediol as the other component was 1,2-propanediol or 1,3-propanediol.

Against yeast (*C. albicans*), the present invention products 1 to 4 and the present invention products 6 to 9 had antimicrobial activities equal to or greater than 1,2-octanediol (comparative product 3) which was used as a control, however, it was found that the present invention product 5 and the present invention product 10 had antimicrobial activities lower than 1,2-octanediol (comparative product 3) which was used as a control.

Further, when the present invention products 3 and 8 as β-hydroxydecanoic acid derivatives were compared with the comparative products 1 and 2, it was found that the present invention product 3 of propanediol type (1,2-propanediol mono-β-hydroxydecanoic acid ester) and the present invention product 8 of propanediol type (1,3-propanediol mono-β-hydroxydecanoic acid ester) exhibited very stronger antimicrobial activities than the comparative product 1 of glycerin ester type (glycerin mono β-hydroxydecanoic acid ester) and the comparative product 2 of potassium salt type (β-hydroxydecanoic acid potassium) against black mold (*A. niger*) and yeast (*C. albicans*).

In addition, the comparative product 4 (1,2-propanediol) and the comparative product 5 (1,3-propanediol), each of which was another component of the present invention products 1 to 10, had lower antimicrobial activities against black mold (*A. niger*) and yeast (*C. albicans*).

C. Antiseptic Property Evaluation Test for Cosmetics (Lotions)

According to a formula shown in Table 2, any one of antimicrobial components selected from the present invention product 8 (1,3-propanediol mono-β-hydroxydecanoic acid ester), the comparative product 1 (glycerin mono β-hydroxydecanoic acid ester), the comparative product 2 (β-hydroxydecanoic acid potassium) and the comparative product 3 (1,2-octanediol) was compounded into a lotion component containing 1,3-butylene glycol, glycerin, polyethylene glycol 1000, POE (60) hydrogenated castor oil and water to prepare lotions (compounding examples 1 to 4) and the antiseptic property of the respective lotion was evaluated by a challenge test (a preservation effectiveness test) to be described later. It is noted that a lotion (compounding example 5) which did not contain any of the above described antimicrobial components was used as a control.

TABLE 2

| Name of Component | Compounded amount (weight %) | | | | |
|---|---|---|---|---|---|
| | Compounding example 1 | Compounding example 2 | Compounding example 3 | Compounding example 4 | Compounding example 5 |
| 1,3-butylene glycol | 6.0 | 6.0 | 6.0 | 6.0 | 6.0 |
| Glycerin | 4.0 | 4.0 | 4.0 | 4.0 | 4.0 |
| Polyethylene glycol 1000 | 1.0 | 1.0 | 1.0 | 1.0 | 1.0 |
| POE (60) hydrogenated castor oil | 0.3 | 0.3 | 0.3 | 0.3 | 0.3 |
| Present invention product 8 | 0.3 | — | — | — | — |
| Comparative product 1 | — | 0.3 | — | — | — |
| Comparative product 2 | — | — | 0.3 | — | — |
| Comparative product 3 | — | — | — | 0.3 | — |
| Water | Remaining part | Remaining part | Remaining part | Remaining part | Remaining part |

Present invention product 8: 1,3-propanediol mono-β-hydroxydecanoic acid ester
Comparative product 1: glycerin mono β-hydroxydecanoic acid ester
Comparative product 2: β-hydroxydecanoic acid potassium
Comparative product 3: 1,2-octanediol As bacteria to be tested, black mold (*A. niger*, JCM10254) was used. A culture solution obtained by previously culturing the bacteria was prepared to contain approximately $10^6$ to $10^7$ cfu/ml of the bacteria, and it was used as a bacterial suspension. The number of the bacteria was determined by a colony count method. 20 g each of the lotions for compounded examples 1 to 5 were put into a 50 ml vial container sterilized by an autoclave, 100 µl of the bacterial suspension was inoculated and cultivation was performed at 25° C. With respect to the remaining number of the bacteria in the test samples, 0.5 g of each of the test samples were taken at the time of the inoculation, after one hour, after one day and after seven days, the solution obtained by dilution with saline solution was applied to an agar medium and cultured for twenty-four hours and the number of the bacteria in the test samples was calculated. The results are shown in FIG. 1.

FIG. 1 shows that in case of the formula of the compounded example 4 in which the comparative product 3 (1,2-octanediol) was compounded, it took fourteen days until black mold died out. However, in case of the formula of the compounded example 1 in which the present invention product (1,3-propanediol mono-β-hydroxydecanoic acid ester) was compounded, it took seven days until black mold died out. The above results show that the compounding example 1 has more excellent antiseptic property against black mold than the compounding example 4.

Further, with regard to antiseptic effects of the compounding examples 2 and 3 in which a β-hydroxydecanoic acid derivative was compounded, the compounding example 2 in which the comparative product 1 (glycerin mono β-hydroxydecanoic acid ester) was compounded and the compounding example 3 in which the comparative product 2 (β-hydroxydecanoic acid potassium) was compounded hardly reduced the number of live bacteria as with a control (the compounding example 5).

The above results show that, of the compounding examples 1 to 5, the compounding example 1 in which the present invention product 8 was compounded has the highest antiseptic effects.

The challenge test in which yeast (*C. albicans*) was used in place of black mold (*A. niger*, JCM10254) also confirmed that the compounding example 1 in which the present invention product 8 was compounded had the highest antiseptic effects.

Further, when lotions in which the present invention products 1 to 3, 6, and 7 were compounded in place of the present invention product 8 were evaluated for antiseptic property by the same method as described above, all the lotions in which the present invention products 1 to 3, 6, and 7 were compounded exhibited antiseptic effects equal to those of the lotion in which the present invention product 8 was compounded.

D. Compounding Property of Cosmetic Composition in which the Antimicrobial Agent of the Present Invention is Compounded

| (Compounding formulation of lotion) | |
|---|---|
| Glycerin | 5.00 weight % |
| Dipropylene glycol (DPG) | 3.00 |
| POE (60) hydrogenated castor oil | 0.60 |
| Citric acid Na | 0.15 |
| Citric acid | 0.01 |
| Glycine | 0.20 |
| Alanine | 0.10 |
| Hyaluronic acid Na | 0.01 |
| 1,3-propanediol mono-β-hydroxydecanoic acid ester | 0.30 |
| Water | Remaining part |

(Formulation Method)

Glycerin, DPG, POE (60) hydrogenated castor oil, and 1,3-propanediol mono-β-hydroxydecanoic acid ester were mixed and dissolved by being heated to 70° C. (the resulting mixture was referred to as a mixture A). On the other hand, citrate acid Na, citric acid, glycine, alanine, hyaluronic acid Na, and water were individually mixed at room temperature (the resulting mixture was referred to as a mixture B). Then, the mixture A and the mixture B were combined and mixed at 50° C., and thus a lotion was obtained.

(Compounding Property)

The 1,3-propanediol mono-β-hydroxydecanoic acid ester was easily mixed with other components. Turbidity or precipitation was not found in the obtained lotion.

| (Compounding formulation of milky lotion) | |
| --- | --- |
| Cetanol | 1.00 weight % |
| Squalane | 4.00 |
| Stearic acid | 1.00 |
| Polyethylene glycol monostearate (25EO) | 3.20 |
| Glycerin stearic acid monoester | 1.00 |
| 1,3-propanediol mono-β-hydroxydecanoic acid ester | 0.30 |
| γ-tocopherol | 0.05 |
| BHT (antioxidizing agent) | 0.01 |
| 1,3-butanediol | 3.00 |
| Carboxy vinyl polymer | 0.20 |
| Potassium hydroxide | 0.20 |
| Purified water | Remaining part |

(Formulation Method)

Cetanol, squalane, stearic acid, γ-tocopherol, BHT, polyethylene glycol monostearate (25EO), glycerin stearic acid monoester, and 1,3-propanediol mono-β-hydroxydecanoic acid ester were individually mixed and dissolved by being heated to 70° C. (the resulting mixture was referred to as a mixture A). On the other hand, 1,3-butanediol, carboxy vinyl polymer, and potassium hydroxide were individually mixed at room temperature (the resulting mixture was referred to as a mixture B). Then, the mixture A and the mixture B were combined and heated to 60° C. and were vigorously stirred and emulsified while being gradually added in small quantities to the purified water, and thus a milky lotion was obtained.

(Compounding Property)

The product according to the present invention was immediately mixed with other components. Separation or precipitation was not found in the obtained milky lotion.

E. Antiseptic Property Evaluation Test for Pharmaceutical Products (Hair Growth Liquids)

According to formulas shown in Table 3, hair growth liquids (compounding examples 6 to 9) were prepared, in which any one of antimicrobial components selected from the present invention product 8 (1,3-propanediol mono-β-hydroxydecanoic acid ester), the comparative product 1 (glycerin mono β-hydroxydecanoic acid ester), the comparative product 2 (β-hydroxydecanoic acid potassium) and the comparative product 3 (1,2-octanediol) was mixed with hair liquid components containing pantothenic acid, hyaluronic acid, thioxolone, hydrocortisone acetate, tocopherol, minoxidil, glycerin, polyoxyethylene glycol monoether, ethanol, and water, and also a hair growth liquid (the compounding example 10) was prepared, in which no antimicrobial components were mixed with hair liquid components containing pantothenic acid, hyaluronic acid, thioxolone, hydrocortisone acetate, tocopherol, minoxidil, glycerin, polyoxyethylene glycol monoether, ethanol and water. The antiseptic property of each of the hair liquid was evaluated by the same method as that of the above description of <C. Antiseptic Property Evaluation Test for Cosmetics (Lotions)> and it was confirmed that the compounding example 6 in which the present invention product 8 was compounded had the highest antiseptic effects.

Further, the antiseptic property of hair liquids in which the present invention products 1 to 3, 6, and 7 were compounded in place of the present invention product 8 was evaluated by the same method as described above. All the hair liquids in which the present invention products 1 to 3, 6, and 7 were compounded exhibited antiseptic effects equal to those of the hair liquid in which the present invention product 8 was compounded.

TABLE 3

| | Compounded amount (weight %) | | | | |
| --- | --- | --- | --- | --- | --- |
| Name of Component | Compounding example 6 | Compounding example 7 | Compounding example 8 | Compounding example 9 | Compounding example 10 |
| Pantothenic acid | 0.10 | 0.10 | 0.10 | 0.10 | 0.10 |
| Hyaluronic acid | 0.10 | 0.10 | 0.10 | 0.10 | 0.10 |
| Thioxolone | 0.02 | 0.02 | 0.02 | 0.02 | 0.02 |
| Hydrocortisone acetate | 0.10 | 0.10 | 0.10 | 0.10 | 0.10 |
| Tocopherol | 0.10 | 0.10 | 0.10 | 0.10 | 0.10 |
| Minoxidil | 0.05 | 0.05 | 0.05 | 0.05 | 0.05 |
| Glycerin | 1.00 | 1.00 | 1.00 | 1.00 | 1.00 |
| Polyoxyethylene glycol monoether | 10.00 | 10.00 | 10.00 | 10.00 | 10.00 |
| Ethanol | 10.00 | 10.00 | 10.00 | 10.00 | 10.00 |
| The present invention product 8 | 0.30 | — | — | — | — |

TABLE 3-continued

| Name of Component | Compounded amount (weight %) | | | | |
|---|---|---|---|---|---|
| | Compounding example 6 | Compounding example 7 | Compounding example 8 | Compounding example 9 | Compounding example 10 |
| Comparative product 1 | — | 0.30 | — | — | — |
| Comparative product 2 | — | — | 0.30 | — | — |
| Comparative product 3 | — | — | — | 0.30 | — |
| Water | Remaining part | Remaining part | Remaining part | Remaining part | Remaining part |

Present invention product 8: 1,3-propanediol mono-β-hydroxydecanoic acid ester
Comparative product 1: glycerin mono β-hydroxydecanoic acid ester
Comparative product 2: β-hydroxydecanoic acid potassium
Comparative product 3: 1,2-octanediol

F. Compounding Property of Pharmaceutical Products (Hair Growth Liquids) in which the Antimicrobial Agent of the Present Invention is Compounded With regard to the compounding example 6, pantothenic acid, hyaluronic acid, thioxolone, hydrocortisone acetate, tocopherol, and minoxidil were mixed individually and dissolved by being heated to 70° C. (the resulting mixture was referred to as a mixture A). On the other hand, glycerin, polyoxyethylene glycol monoether, ethanol, and the present invention product 8 (1,3-propanediol mono-β-hydroxydecanoic acid ester) were mixed at room temperature (the resulting mixture was referred to as a mixture B). Then, the mixture A and the mixture B were combined and heated to 70° C. and were vigorously stirred while being added gradually in small quantities to water, and thus a hair growth liquid was obtained.

The present invention product (1,3-propanediol mono-β-hydroxydecanoic acid ester) was easily mixed with other components. Turbidity or precipitation was not found in the obtained hair liquid.

G. Antiseptic Property Evaluation Test for Industrial Products (Transparent Aqueous Aromatic Agents for Vehicles)

According to formulas shown in Table 4, transparent aqueous aromatic agents for vehicles (compounding examples 11 to 14) were prepared, in which any one of antimicrobial compositions selected from the present invention product 8 (1,3-propanediol mono-β-hydroxydecanoic acid ester), the comparative product 1 (glycerin mono β-hydroxydecanoic acid ester), the comparative product 2 (β-hydroxydecanoic acid potassium) and the comparative product 3 (1,2-octanediol) were mixed with aromatic agent components containing polyoxyethylene nonylphenyl ether, polyoxyethylene sorbitan monosterate, BHT, fragrant material, gellan gum, propylene glycol, and water, and also a transparent aqueous aromatic agent for vehicles (compounding example 15) was prepared, in which no antimicrobial components were mixed with aromatic agent components containing polyoxyethylene nonylphenyl ether, polyoxyethylene sorbitan monosterate, BHT, fragrant material, gellan gum, propylene glycol, and water. The antiseptic property of each aromatic agent was evaluated by the same method as that of the above description of <C. Antiseptic Property Evaluation Test for Cosmetics (Lotions)> and it was confirmed that the compounding example 11 in which the present invention product 8 was compounded had the highest antiseptic effects.

Further, the antiseptic property of aromatic agents in which the present invention products 1 to 3, 6, and 7 were compounded in place of the present invention product 8 was evaluated by the same method as described above. All the aromatic agents in which the present invention products 1 to 3, 6, and 7 were compounded exhibited antiseptic effects equal to those of the aromatic agent in which the present invention product 8 was compounded.

TABLE 4

| Name of Component | Compounded amount (weight %) | | | | |
|---|---|---|---|---|---|
| | Compounding example 11 | Compounding example 12 | Compounding example 13 | Compounding example 14 | Compounding example 15 |
| Polyoxyethylene nonylphenylether | 8.0 | 8.0 | 8.0 | 8.0 | 8.0 |
| Polyoxyethylene sorbitan monosterate | 2.0 | 2.0 | 2.0 | 2.0 | 2.0 |
| BHT | 0.1 | 0.1 | 0.1 | 0.1 | 0.1 |
| Fragrant material | 3.0 | 3.0 | 3.0 | 3.0 | 3.0 |
| Gellan gum | 0.7 | 0.7 | 0.7 | 0.7 | 0.7 |
| Propylene glycol | 3.0 | 3.0 | 3.0 | 3.0 | 3.0 |
| Present invention product 8 | 0.30 | — | — | — | — |

TABLE 4-continued

| Name of Component | Compounded amount (weight %) | | | | |
|---|---|---|---|---|---|
| | Compounding example 11 | Compounding example 12 | Compounding example 13 | Compounding example 14 | Compounding example 15 |
| Comparative product 1 | — | 0.30 | — | — | — |
| Comparative product 2 | — | — | 0.30 | — | — |
| Comparative product 3 | — | — | — | 0.30 | — |
| Water | Remaining part | Remaining part | Remaining part | Remaining part | Remaining part |

Present invention product 8: 1,3-propanediol mono-β-hydroxydecanoic acid ester
Comparative product 1: glycerin mono β-hydroxydecanoic acid ester
Comparative product 2: β-hydroxydecanoic acid potassium
Comparative product 3: 1,2-octanediol H. Compounding Property of Industrial Products (Transparent Aqueous Aromatic Agents for Vehicles) in which the Antimicrobial Agent of the Present Invention is Compounded In preparing the compounding example 11, polyoxyethylene nonylphenylether, polyoxyethylene sorbitan monosterate, BHT, and fragrant material were mixed individually and dissolved by being heated to 80° C. (the resulting mixture was referred to as a mixture A). On the other hand, gellan gum, propylene glycol, the present invention product 8 (1,3-propanediol mono-β-hydroxydecanoic acid ester), and water were mixed at 80° C. (the resulting mixture was referred to as a mixture B). Then, the mixture B was gradually added in small quantities to the mixture A, heated to 80° C., and were vigorously stirred, and thus a transparent aqueous aromatic agent for vehicles was obtained.

The present invention product 8 (1,3-propanediol mono-β-hydroxydecanoic acid ester) was easily mixed with other components. Turbidity or precipitation was not found in the obtained aromatic agent.

INDUSTRIAL APPLICABILITY

The antimicrobial agent of the present invention has excellent antimicrobial activity against fungi and also has excellent compounding property. Thus, the antimicrobial agent is preferable as an antiseptic component for items to be antisepticized such as food, cosmetics, pharmaceutical products, medical devices, and industrial products.

What is claimed is:

1. A composition comprising an antimicrobial agent of Formula 1 or Formula II wherein the antimicrobial agent of Formula I is prepared from a 1,2-propanediol and the antimicrobial agent of Formula II is prepared from a 1,3-propanediol

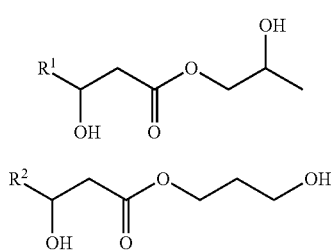

wherein $R^1$ and $R^2$ are both branched or unbranched, and saturated or unsaturated $C_5$ to $C_9$ alkyl groups,
wherein the antimicrobial agent provides improved antimicrobial activity against *A. niger* and *C. albicans* and the antimicrobial agent is present in an amount of 0.1 to 10 wt %.

2. The composition according to claim 1, wherein $R^1$ and $R^2$ are both unbranched and saturated or unsaturated $C_7$ to $C_9$ alkyl groups.

3. A cosmetic product which contains the antimicrobial agent according to claim 1.

4. A non-therapeutic product or composition for improved antiseptic activity selected from the group consisting of cosmetic, food, pharmaceutical product, medical device, industrial product, tableware, clothing, paint, and pet hygiene products comprising the antimicrobial agent according to claim 1.

5. A cosmetic product which contains the antimicrobial agent according to claim 2.

6. A non-therapeutic product or composition for improved antiseptic activity selected from the group consisting of cosmetic, food, pharmaceutical product, medical device, industrial product, tableware, clothing, paint, and pet hygiene products comprising the antimicrobial agent according to claim 2.

7. A composition comprising an antimicrobial agent of Formula VI:

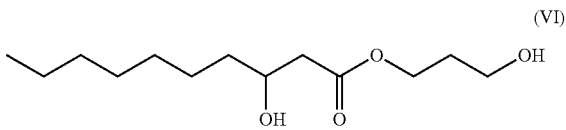 [SMILES: CCCCCCCC(O)CC(=O)OCCCO]

wherein the antimicrobial agent provides improved antimicrobial activity against *A. niger* and *C. albicans* and the antimicrobial agent is present in an amount of 0.1 to 10 wt %.

8. A cosmetic product which contains the antimicrobial agent according to claim 7.

9. A non-therapeutic product or composition for improved antiseptic activity selected from the group consisting of cosmetic, food, pharmaceutical product, medical device, industrial product, tableware, clothing, paint, and pet hygiene products comprising the antimicrobial agent according to claim 7.

* * * * *